(12) United States Patent
Shrivastava

(10) Patent No.: US 6,964,783 B1
(45) Date of Patent: Nov. 15, 2005

(54) NON-SOLID COMPOSITION FOR LOCAL APPLICATION

(75) Inventor: Ravi Shrivastava, Cebazat (FR)

(73) Assignee: Naturveda, Sainte Florine (FR)

( * ) Notice: Subject to any disclaimer, the term of this patent is extended or adjusted under 35 U.S.C. 154(b) by 0 days.

(21) Appl. No.: 10/009,027

(22) PCT Filed: Jun. 8, 1999

(86) PCT No.: PCT/FR99/01340

§ 371 (c)(1),
(2), (4) Date: Jul. 1, 2002

(87) PCT Pub. No.: WO00/74668

PCT Pub. Date: Dec. 14, 2000

(51) Int. Cl.⁷ .......................................... A61K 35/78
(52) U.S. Cl. ................................................. 424/725
(58) Field of Search ..................................... 424/725

(56) References Cited

U.S. PATENT DOCUMENTS

| | | | | |
|---|---|---|---|---|
| 4,054,649 A | * | 10/1977 | Cariel | .......................... 424/764 |
| 4,397,944 A | * | 8/1983 | Komura et al. | ................. 435/4 |
| 4,722,843 A | * | 2/1988 | Vinson | ......................... 424/401 |
| 5,133,973 A | * | 7/1992 | Paradies | ...................... 424/450 |
| 5,411,993 A | * | 5/1995 | Yamamoto et al. | .......... 514/766 |
| 6,395,309 B1 | * | 5/2002 | Franz et al. | ................. 424/725 |
| 6,656,460 B2 | * | 12/2003 | Benita et al. | ............. 424/78.04 |

FOREIGN PATENT DOCUMENTS

| | | |
|---|---|---|
| EP | 579 155 | 1/1994 |
| FR | 2 332 026 | 6/1977 |
| WO | 98/03152 | 1/1998 |

OTHER PUBLICATIONS

Database WPI; XP-002130212; Derwent Publications Ltd.; Intr. Medicamente Biofarm.; Oct. 1983.

* cited by examiner

Primary Examiner—Herbert J. Lilling
(74) Attorney, Agent, or Firm—Merchant & Gould P.C.

(57) ABSTRACT

The invention concerns a composition, in particular a non-solid pharmaceutical composition for local application comprising, as active principle, at least glycerol or a concentrated solution of glycerol, saccharose, sorbitol or mannitol, the active principle concentration of said composition being osmotically active towards plasma.

7 Claims, No Drawings

NON-SOLID COMPOSITION FOR LOCAL APPLICATION

The present invention relates to new non-solid, particularly pharmaceutical, formulation containing a hypertonic solution or glycerine, and their use for the treatment of aphthae and surface wounds.

The development of lesions in the form of aphthae in the mouth and occasionally on other parts of the body is a very frequent complaint. Most subjects are liable to develop aphthae in the mouth and suffer from small wounds. Although aphthae do not represent a disease in themselves, they are the cause of considerable pain and significant discomfort.

From a physiopathological viewpoint, an aphtha may be considered as a localised rupture of the integrity of the surface areas of the skin or mucous membranes. This wound exposes underlying and deeper tissue to more extensive trauma, which results in the bursting of vessels and the damage of parts deeper than the mucous membrane or epidermis. These small wounds are exposed to micro-organisms, in particular bacteria responsible for secondary infections, such as streptococci and staphylococci, which secondarily induce deeper lesions in the form of mouth ulcers.

The development of such lesions on the skin is associated with traumatic wounds and itching, but aphtha formation on mucous membranes may also be linked with other factors which are not fully known at the present time. In addition to traumatic lesions, the occurrence of aphthae and mouth ulcers may also be due to certain components of the diet which modify the mucous membranes. Deficiency in certain vitamins, such as vitamin A, represents a cause of fragility of the mucous membrane which is easily ruptured following small wounds.

Clinically, aphthae or surface wounds are small lesions of the mucous membranes or epidermis (from a few millimeters to a few centimeters), purple or yellowish in colour, which expose underlying layers of tissue and capillary blood vessels. These lesions represent an ideal site for bacterial proliferation. The presence of pyrogenic bacteria is a common phenomenon. The body's defence system and regeneration process are immediately activated after wound formation and start the healing process. The immune system fights against bacterial and infectious proliferation to prepare the damaged area for regeneration phenomena.

Although these processes are relatively rapid for skin wounds, it takes at least seven to tens for mouth aphthae to be completely healed. This considerable remission period is linked to the fact that the aphthae are in constant contact with food which contains non-pathogenic germs. In this way, the wounded area is constantly exposed to micro-organisms ready to multiply in a favourable environment. Constant movements inside the mouth, for example during speech, also increase the time required for regeneration and delay wound repair.

The treatments currently available consist of stopping or reducing bacterial multiplication on the wound without favouring tissue regeneration prior to healing. Most of the treatments available for aphthae contain antibiotics or antiseptic agents. These treatments consist of local applications. In the case of severe infections, oral antibiotic therapy is used. A major drawback of these treatments is that they only act on the wound's secondary bacterial infections but do not have any direct activity on tissue regeneration.

Frequently, the wounded subject tends to scratch the wounded area, which induces inflammation and may aggrevate the extent of the lesions. In this way, another non-negligible drawback of the treatments currently available is that they do not reduce the remission time of wounded subjects who continue to feel highly discomforting pain and may worsen already considerable wounds.

These treatments also have side effects, common to antibiotic therapies.

In this way, an ideal treatment for aphthae should have three main qualities:

Eliminate the micro-organisms present on the wounds, in order to create a favourable environment for cell multiplication.

Accelerate tissue regeneration to accelerate healing and reduce the remission time as much as possible.

Be non-toxic and not cause side effects.

To date, no product offering all three properties, consisting of eliminating bacteria from the wound, healing in addition to a lack of toxicity, has been discovered.

Glycerine or concentrated solutions, for example concentrated sugar solutions, have frequently been used as a preservative, such as in jams, or as excipients, but no pharmacological activity, particularly for the treatment of aphthae or surface wounds, has ever been described for these products.

However, the applicant was surprised to discover that bacteria could be eliminated from the open wound in a very short time by applying a concentrated solution, osmotically active with respect to plasma, and that, in addition, the time required to obtain healing was considerably reduced due to the use of a substance which increases cell multiplication.

For this reason, the present application relates to a non-solid, preferentially liquid, formulation for local application which comprises, as an active ingredient, at least glycerol or a concentrated solution of glycerol, sucrose, sorbitol or mannitol, the active ingredient concentration of said non-solid formulation being osmotically active with respect to plasma, particularly blood plasma.

Under preferential embodiment conditions of the invention, the non-solid formulation is a pharmaceutical formulation.

In the present application and below, the term "non-solid" applied to a formulation according to the invention refers to both liquid and semi-liquid (viscous) preparations.

According to the applicant's observations, pure glycerol or a concentrated solution of sucrose, sorbitol, mannitol or glycerine (glycerol), applied to an open surface wound induces a drainage and healing acceleration phenomenon. This drainage mechanism is the result of osmotic phenomena, inflammatory and humoral (vasodilation) and immune (migration of immunocompetent cells to the wounded site) reactions, which are not known in detail. Under the influence of diffusion laws, the glycerol or hypertonic solution would tend to penetrate into the tissue. However, this penetration is limited by the size of the molecules which cannot reach the blood circulation. However, the plasma present on the damaged capillary vessels which show an increased permeability, is exuded to the wound in order to restore the osmotic balance. In this way, the application of a concentrated hypertonic solution on the wound induces the exudation of a large quantity of plasma. During this process, the micro-organisms present on the wound are eliminated with the plasma flow, which rapidly reduces the bacterial concentration. In this way, concentrated solutions enable drainage of small wounds such as aphthae and surface wounds.

This plasma exudation also provides numerous immune factors (immunoglobulins, complement system, leukocytes, etc.) which also take part in the elimination of the bacteria, which creates a favourable environment for the healing of the wound.

In addition, glycerol or concentrated solutions of sucrose, sorbitol, mannitol, glycerine (glycerol) show a very low toxicity or are even harmless for health and can be used by the oral route, without inducing any side effects.

Under preferential embodiment conditions of the invention, glycerol, particularly pure, is used as the active ingredient in the non solid formulation. Sorbitol or mannitol are also preferentially used in the non-solid formulation according to the invention.

Under other preferential embodiment conditions of the invention, the active ingredient concentration in the non-solid formulation must make it possible to obtain a solution with an osmotic power greater than that of plasma, i.e. greater than 300 milliosmoles (mOsm), preferentially greater than 500 mOsm, particularly greater than 800 mOsm, and more particularly greater than 1 Osm. It is understood that at least 30%, preferentially at least 60%, particularly at least 80%, particularly at least 90%, and more particularly at least 95% of said osmotic power is provided by said active ingredient, with the remainder of the osmotic power possibly provided by other osmotically active compounds.

Under further preferential embodiment conditions of the invention, the active ingredient concentration in the non-solid formulation is such that the quantity of diluent (solvent) by volume is less than 70%, preferentially less than 40%, particularly less than 20% and more particularly less than 10%.

Mixing the above osmotically active substances with antibiotic or antiseptic products of synthetic or natural origin makes it possible to increase the antibacterial effect. Mixing the above osmotically active substances with a compound having cell proliferation stimulant properties also increases the healing rate of the wound.

For these reasons, the present application also relates to a non-solid formulation as described above wherein at least one osmotically active substance is associated with at least one antiseptic product or one product stimulating cell multiplication. Such an association represents an effective solution for the treatment of aphthae, surface wounds, burns, and postoperative care, in order to stimulate healing while reducing scars.

In this way, it is particularly possible to find in the non-solid formulations according to the invention, one or more substances capable of stimulating cell proliferation, and particularly plant extracts conventionally used or not in the treatment of dermatological disorders (*Mimosa tenuiflora, Quercus, Aesculus hippocastanum, Geranium robertianum, Cupressus sempervirens, Vitis vinifera, Ribes nigrum, Centella asiatica, Matricaria Chamomilla* and more particularly *Alchemilla Vulgaris*), or any other substance with a "growth factor" type activity (e.g. esoin, procyanidolic tannins-oligomers, mimosides) or also at least one antibiotic, bacteriostatic or bactericide (e.g. papain, geraniin).

These particularly pharmaceutical formulations may be, for example, liquid or semi-liquid and come in the pharmaceutical forms generally used in human medicine, such as for example solutions in tubes with an elongated tip or in a spray; they are prepared according to the usual methods. The active ingredient(s) may be incorporated into excipients generally used in pharmaceutical formulations, such as aqueous or non-aqueous vehicles, various wetting agents, preservatives, thickening agents.

The invention also relates to glycerol or a concentrated solution of glycerol, sucrose, sorbitol or mannitol, at an osmotically active concentration with respect to plasma, for their use for a therapeutic treatment method for the human body or animals, i.e. as a medicinal product.

The medicinal products according to the present invention find applications for example in the curative and preventive treatment of aphthae. They also find applications in the treatment of ulcers of the mucous membranes or the epidermis other than aphthae.

The standard dose, which may vary according to the subject treated and the disorder at cause, may be, for example, 2 applications to 6 applications per day locally in humans of 2 drops of formulation according to example 3 on each aphtha, for 3 days.

The present invention also relates to a method to prepare the formulation described above, characterised in that the active ingredient(s) are mixed, using known methods, with acceptable, particularly pharmaceutically acceptable, excipients or solvents.

The invention finally relates to the use of glycerol or a concentration solution of glycerol, sucrose, sorbitol or mannitol, at an osmotically active concentration with respect to plasma, to obtain a medicinal product intended to treatment small lesions of the mucous membranes or epidermis, particularly aphthae.

The preferential embodiment conditions of the non-solid, preferentially liquid, formulations described above also apply to the other purposes of the invention mentioned above.

The examples below illustrate the present application.

EXAMPLE 1

10 ml tubes with 4 cm tips complying with the following formula were prepared:

| | |
|---|---|
| Water | 60 ml |
| Sorbitol | 40 g |

Stir until completely dissolved.

EXAMPLE 2

10 ml tubes with 4 cm tips complying with the following formula were prepared:

| | |
|---|---|
| Water | 50 ml |
| Glycerol | 50 ml |

EXAMPLE 3

10 ml tubes with 4 cm tips complying with the following formula by weight were prepared:

| | |
|---|---|
| Water | 45% |
| Xanthanum gum | 0.5% |
| Methyl parahydroxybenzoate | 0.15% |
| Hydroalcoholic alchemilla extract* | 5% |
| Blackcurrant flavour | 0.43% |
| Glycerol | up to 100% |

*Source BIOSPHERE - FRANCE: 150 g of dry leaves in 500 ml of water and 500 ml of ethanol.

EXAMPLE 4

10 ml tubes with 4 cm tips complying with the following formula were prepared:

| | |
|---|---|
| Glycerine | 97 ml |
| Dry Alchemilla vulgaris extract | 3 g |

Mix.

EXAMPLE 5

10 ml tubes with 4 cm tips complying with the following formula were prepared:

| | |
|---|---|
| Glycerol | 90% |
| Blackcurrant extract | 9% |
| Azadirachta indica extract | 1% |

Mix.

EXAMPLE 6

10 ml tubes with 4 cm tips complying with the following formula were prepared:

| | |
|---|---|
| Glycerine | 96.5% |
| Typical Alchemilla vulgaris extract | 3% |
| Azadirachta indica extract | 0.5% |

EXAMPLE 7

Tubes of different capacities complying with the following formula were prepared:

| | |
|---|---|
| Horse chestnut extract | 8.1% |
| Cypress extract | 5.0% |
| Geranium robertianum extract | 4.0% |
| Escin | 0.3% |
| Papain | 0.1% |
| Carbomer | 0.5% |
| Alcohol | 4.0% |
| Phenonip | 0.5% |
| PEG-7 Glyceryl cocoate | 3.0% |
| Glycerol | 30% |
| Water up to | 100% |

EXAMPLE 8

Tubes of different capacities complying with the following formula were prepared:

| | |
|---|---|
| Alchemilla vulgaris | 9.8% |
| Red vine | 2.0% |
| Mimosa tenuiflora | 5.0% |
| Carbomer | 0.4% |
| PEG-7 Glyceryl cocoate | 2.0% |
| Phenonip | 0.5% |
| Triethanolamine | 0.2% |

| | |
|---|---|
| Fragrance | 0.2% |
| Glycerol | 10–40% |
| Water up to | 100% |

EXAMPLE 9

Tubes of different capacities complying with the following formula were prepared:

| | |
|---|---|
| Quercus extract | 0.5% |
| Escin | 0.1% |
| Azadirachta indica | 1.1% |
| Methyl parahydroxybenzoate | 0.15% |
| Xanthanum gum | 0.5% |
| Blackcurrant extract | 0.43% |
| Glycerol | 50% |
| Water up to | 100% |

Pharmacological Study

Effect of Glycerine Associated with a Plant Extract Conventionally Used in the Treatment of Dermatological Disorders 30 rats (IFFA-CREDO SPF weighing 200+/−20 g) were shaved (3×3 cm) on the right side of the back. A 0.4×0.4 cm wound was produced at the centre of the shaved area. 30 minutes after producing the small wound, the coagulated blood was removed and 0.2 ml of glycerine containing 3% *Alchemilla vulgaris* (preparation according to example 4) or 0.2 ml of pure glycerine (controls) were applied on ten animals. The ten other control rats received 0.2 ml of distilled water. The complete healing time and the healing index were determined each day for 10 days. The healing time was reduced by 48% with the treatment based on glycerine containing 3% *Alchemilla vulgaris,* with a healing index of 2.1 in the treated lot, compared to an index of 3.3 obtained with the control lot.

With glycerine alone, the healing time was reduced by 26% with a healing index of 2.7. These results indicate that glycerine alone favours the healing of wounds, and also that an association with a product capable of stimulating cell mitosis considerably increases the healing rate.

The effects of different plant extracts on the epithelial cell proliferation rate were determined in vitro. Bovine kidney cells (MDBK) were cultured in 96-well plates ($10^5$ cells/ml; 100 μl per well).

Different plant extract concentrations were added to the culture medium during the preparation of the cells (n=16 per concentration). The cells were incubated for 72 hours (37° C.; 5% CO2) and the total number of cells was determined after trypsinisation and MTT staining.

Only 8 plant extracts out of 26 studied stimulate mitosis by more than 12% in the following order: *Alchemilla vulgaris, Mimosa tenuiflora, Quercus, Aesoulus hippoonstanum, Geranium robertianum, Cupressus sempervirens, Vitis vinifera, Ribes nigrum.*

Clinical Study

Firstly, a preparation containing 97% glycerine and 3% of a hydroalcoholic *Alchemilla vulgaris* extract (3% dry plant extract w/w), according to example 4, and secondly, a preparation containing 97% ethanol at 96% and 3% of a hydroalcoholic *Alchemilla vulgaris* extract (3% dry plant extract w/w) were placed in 10 ml tubes.

18 subject suffering regularly from mouth aphtha problems were enrolled in the pilot clinical study. 8 control subjects tested the hydroalcoholic extract while 10 subjects tested the hydroglycerine extract. Two drops of product were applied 3 times a day after meals until complete healing. The time required to obtain a complete remission was determined with both groups.

The mean healing time is 2.7 days in the group treated with the hydroglycerine extract compared to 6.3 days with the control group.

The use of osmotically active substances or glycerine, alone or in association with other compounds stimulating cell mitosis, improves cell proliferation, surface wound healing and, particularly, aphtha healing phenomena.

What is claimed is:

1. A viscous composition for topical application for the treatment of ulcers or superficial injuries comprising:
   glycerol as active principle, and
   a hydroalcoholic extract of *Alchemilla vulgaris* as a cell growth agent,
   the composition being osmotically active compared to blood plasma.

2. A viscous composition for topical application according to claim 1 wherein the composition has an osmotic strength greater than 300 milliosmoles (mOsm).

3. A viscous composition for topical application according to claim 2 wherein the composition has an osmotic strength greater than 500 milliosmoles (mOsm).

4. A viscous composition for topical application according to claim 1 wherein the concentration of active principle in the viscous composition is such that the quantity of diluant (solvent) is less than 70% by volume.

5. A viscous composition for topical application according to claim 4 wherein the concentration of active principle in the viscous composition is such that the quantity of diluant (solvent) is less than 20% by volume.

6. A viscous composition for topical application according to claim 1 wherein the composition is a pharmaceutical preparation or an oral hygiene product.

7. A method of treating oral ulcers or skin injuries in a subject comprising administering to the subject in need thereof a therapeutic amount of the viscous composition for topical application according to claim 1.

* * * * *